United States Patent [19]

Cueman et al.

[11] Patent Number: 5,738,639
[45] Date of Patent: Apr. 14, 1998

[54] TREATED CORE FOR FACILITATING ORTHOPEDIC CASTING

[75] Inventors: Glenn F. Cueman; Henry L. Richbourg, Jr., both of Davidson; Tony A. Williamson, Troutman, all of N.C.

[73] Assignee: Clinitex Medical Corporation, Huntersville, N.C.

[21] Appl. No.: 642,625

[22] Filed: May 3, 1996

[51] Int. Cl.$^6$ ............................................. A61F 5/00
[52] U.S. Cl. ........................................... 602/6; 602/1; 602/8
[58] Field of Search ........................... 602/3, 5, 6, 8, 602/52, 75, 76, 61, 62, 77, 903, 904, 1; 604/304, 307; 138/DIG. 7

[56] References Cited

U.S. PATENT DOCUMENTS

| | | | |
|---|---|---|---|
| 2,964,174 | 12/1960 | Litchfield et al. | 206/59 |
| 3,062,370 | 11/1962 | Morin | 206/63.2 |
| 3,152,692 | 10/1964 | Johnston | 206/59 |
| 3,630,194 | 12/1971 | Boardman | 128/90 |
| 4,020,832 | 5/1977 | Kirkpatrick et al. | 128/90 |
| 4,131,114 | 12/1978 | Kirkpatrick et al. | 128/90 |
| 4,153,052 | 5/1979 | Tsuk | 128/90 |
| 4,344,423 | 8/1982 | Evans et al. | 128/90 |
| 4,376,438 | 3/1983 | Straube et al. | 128/90 |
| 4,411,262 | 10/1983 | Von Bonin et al. | 128/90 |
| 4,433,680 | 2/1984 | Yoon | 128/90 |
| 4,498,467 | 2/1985 | Kirkpatrick et al. | 128/90 |
| 4,502,479 | 3/1985 | Garwood et al. | 128/90 |
| 4,667,661 | 5/1987 | Scholz et al. | 128/90 |
| 4,774,937 | 10/1988 | Scholz et al. | 128/90 |
| 4,960,116 | 10/1990 | Milner | 128/90 |
| 5,061,555 | 10/1991 | Edenbaum et al. | 428/253 |
| 5,250,344 | 10/1993 | Williamson et al. | 428/143 |
| 5,476,440 | 12/1995 | Edenbaum | 602/8 |
| 5,514,080 | 5/1996 | Blatt et al. | 602/5 |

*Primary Examiner*—Corrine M. McDermott
*Assistant Examiner*—Cris L. Rodriguez
*Attorney, Agent, or Firm*—Dougherty & Dremann

[57] ABSTRACT

A system for improving the handling of a resin coated substrate for molding and smoothing into an orthopedic cast includes a core which is coated with a substance which is substantially inert to the resinous prepolymer in a sealed storage pouch. Water, used to activate the resinous prepolymer, carries the coating to the surface of the substrate, thereby improving handling during the molding process. During normal operation, the cast applier removes the resin coated or impregnated substrate from the storage container and dips it in a water bath to initiate the polymerization process. After removal from the water bath, the applier wraps the substrate around a patient's limb and molds and smooths the substrate to form an orthopedic cast. Once the core about which the resin coated substrate is wrapped is exposed to water, the lubricant is transferred by the water to the outside portion of the cast tape, reducing the tackiness of the cast tape, thereby facilitating its overall handling. This transfer is very limited in nature, and only puts the lubricant in contact with the cast tape at the point which will be used to form the outer most layer of the cast.

9 Claims, 2 Drawing Sheets

5,738,639

TREATED CORE FOR FACILITATING ORTHOPEDIC CASTING

FIELD OF THE INVENTION

The present invention relates to a method of applying an orthopedic cast having a substrate and a water activated tacky resinous pre-polymer, all wrapped about a core containing a water dispersable lubricant which facilitates the molding of the cast, and the apparatus which makes this possible.

BACKGROUND OF THE INVENTION

The current preferred casting systems for orthopedic casts include high strength cast tapes which employ a substrate with a water activated tacky resinous pre-polymer. An example of this type of system is Garwood, et al, U.S. Pat. No. 4,502,479 using a high modulus fiber, preferably fiberglass or applicants' co-pending U.S. patent application Ser. No. 08/639,271, which employs an optimized low modulus fiber substrate. The majority of these systems use a water curable isocyanate-functional pre-polymer which begins rapid polymerization upon exposure to moisture, either atmospheric or the recommended water activation agent. Once these casting materials are removed from their storage containers, and especially after exposure to water used to initiate curing of the pre-polymer, the resins which start out tacky aggressively increase in tackiness until the polymerization process is terminated or cured. The tackiness of the resin laden substrate makes it difficult for the cast applier to apply the substrate for molding and smoothing to a patient's limb because the tacky resin tends to stick to the protective gloves worn by the applier. After the cast is wrapped, but before the cast hardens, some time is necessary in order to mold the cast to fib the limb. This is accomplished by smoothing the cast with a gloved hand as well as supporting the cast at other times until a polymerization process is completed. When using a substrate coated with a tacky resin, the molding of the cast is difficult. The reason for this difficulty is the glove sticks to the resin and when attempts are made to smooth the cast to form it, the layers of tape pull away from each other, thus requiring reforming of part of the cast.

DESCRIPTION OF THE PRIOR ART

Applicant is aware of the following U. S. Patents which are related to improving the handling of the resinous substrate before the curing of the final cast.

| U.S. Pat. No. | Inventor | Issue Date | Title |
| --- | --- | --- | --- |
| 4,774,937 | Scholz et al. | 10-04-19 | CURABLE RESIN COATED SHEET HAVING REDUCED TACK |
| 5,250,344 | Williamson | 10-15-1993 | CAST MATERIAL WITH ENCAPSULATED LUBRICANT |
| 5,476,440 | Edenbaum | 12-19-1995 | ORTHOPEDIC BANDAGE WITH LUBRICOUS CORE |

Scholz, et al, U.S. Pat. No. 4,774,937 teaches a lubricant which is bonded to the prepolymer resin. Williamson, et al U.S. Pat. No. 5,250,344 teaches the deposition of microencapsulated lubricating or friction reducing material directly onto the substrate of the orthopedic cast tape.

Edenbaum U.S. Pat. No. 5,476,440 teaches an encapsulation of a bis-urethane lubricant within a water permeable core released by applying force to the exterior surface of the core to improve handling of the tacky resinous substrate.

SUMMARY OF THE INVENTION

The present invention provides a system for improving the handling of a resin coated or resin impregnated substrate for molding and smoothing into an orthopedic cast. The system includes a core which is coated with a substance which is substantially inert to the resinous prepolymer in a sealed storage pouch, however, the substance is carried by the water, used to activate the resinous prepolymer, to the surface of the substrate, thereby improving handling over the molding process. During normal operation, the cast applier removes the resin coated or impregnated substrate from the storage container, or pouch, and dips it in a water bath to initiate the polymerization process. After removal from the water bath, the applier then wraps the substrate around the patient's limb and molds and smooths the substrate to form an orthopedic cast. Once the core about which the resin coated substrate is wrapped is exposed to water, the lubricant is transferred by the water to the outside portion of the cast tape, reducing the tackiness of the cast tape, thereby facilitating its overall handling. This transfer is very limited in nature and only puts the lubricant in contact with the cast tape at the point which will be used to form the outer most layer of the cast.

OBJECTS OF THE INVENTION

The principal object of the present invention is to provide an improved method of wrapping and molding an orthopedic cast which reduces the tack of the resin coated substrate.

A further object of the invention is to provide a method of molding and smoothing an orthopedic cast which is less tacky and does not appreciably alter the process being utilized by the doctor in the forming of the cast.

Another object of the invention is to provide apparatus for the core which contains or which the lubricant is coated to the outside surface which facilitates the molding and smoothing of the orthopedic cast.

Another object of the invention is to provide a core lubricant which reduces tack but does not interact with the prepolymer system and therefore does not reducing the overall strength of the orthopedic cast.

Another object of the invention is to provide a core lubricant which is non-toxic and will not cause skin irritation.

BRIEF DESCRIPTION OF THE DRAWINGS

The foregoing and other objects will become more readily apparent by referring to the following detailed description and the appended drawings in which.

3

Figure 7:
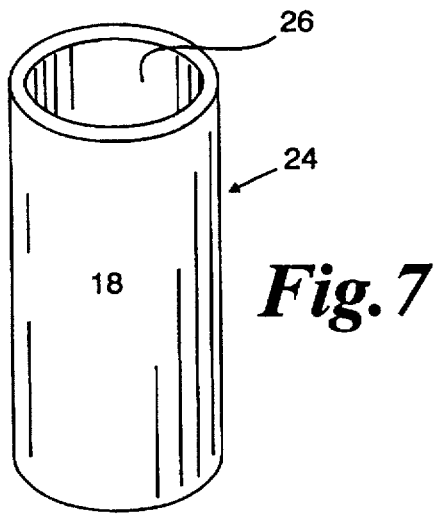

FIG. 7 is an isometric view of an alternative core showing a tubular configuration.

Figure 8:
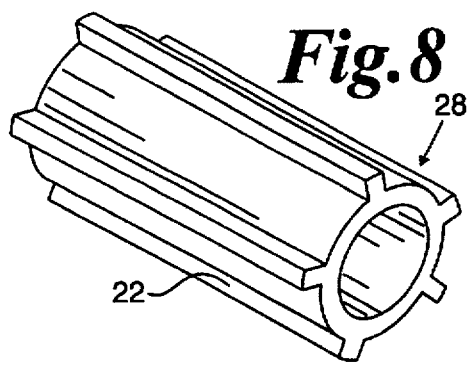

FIG. 8 is an isometric view of another alternative core showing a tubular configuration.

Figure 6:
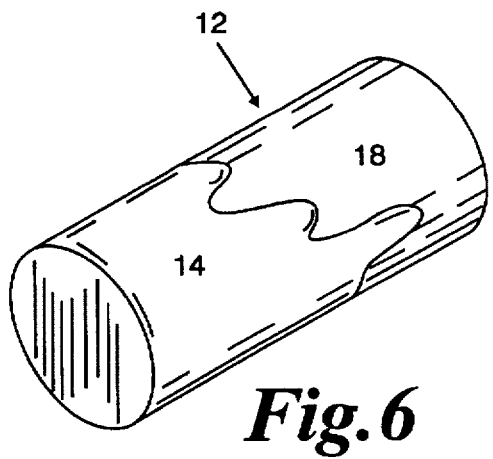
FIG. 6 is an isometric view of an alternative core showing a cut away view of the film of the water soluble agent.
Figure 9:
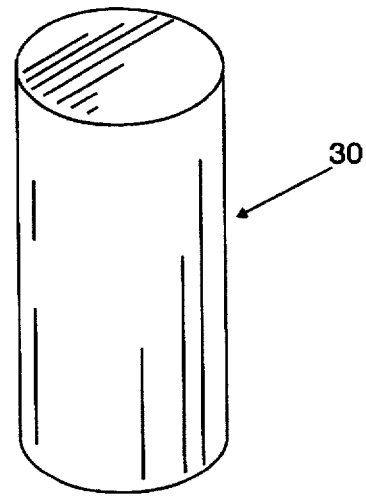

FIG. 9 is an isometric view of the alternative core of FIG. 6.

DETAILED DESCRIPTION

Figure 1:
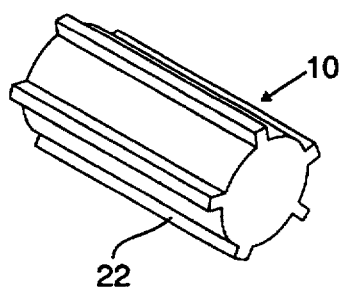
FIG. 1 is an isometric view of a preferred embodiment of the invented core.

Referring now to the drawings, and particularly to FIG. 1, the invented elongated core 10 is preferably molded from a synthetic material. Suitable examples of such material include, but are not limited to, polyester, polypropylene, nylon, aramid, polyethylene, polytetrafluoroethylene, polyvinylchloride, polyvinylidiinechloride, acrylic, polystyrene, polyethylene terephthalate, polyurethane, ureaformaldehyde, phenolics, melamine formaldehydes, modified terephthalates and combinations thereof. Alternatively, the core could be fabricated out of wood, metal, wax or a composite material.

Figure 2:
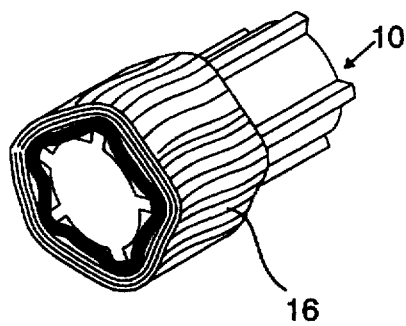
FIG. 2 is a fragmentary view illustrating the core and resin coated substrate of the present invention.

The orthopedic casting material of the present invention comprises an elongated core 12, FIG. 6, coated with a water soluble agent 14, a fabric substrate 16, FIG. 2, wrapped about the core, and a reactive fluid prepolymer resin in contact with the fabric.

The core provides surface area 18, FIG. 6, that can be coated with a material 14 which is inert to reactive fluid prepolymer resin but soluble in water. The preferred water soluble agents are soaps, defined as alkali salts of fatty acids, and detergents, which are defined as compounds having a hydrophobic hydrocarbon end plus a sulfonate or sulfate ionic end. Some examples of alkali salts of fatty acids which can be used include, but are not limited to, sodium lauryl sulfate, sodium stearate, sodium palmitate and combinations thereof.

The elongated core is dipped into an active solution of soap (or detergent) and water, then is removed from the solution. The core is stood on one end for about twenty four (24) hours and allowed to drain. While the core stands, the water of the solution evaporates leaving a thin film of soap 20, FIG. 5, on the surface of the core. Evaporation of the water from the solution-dipped core can be carried out at either room temperature or an elevated temperature. The average amount of sodium lauryl sulfate added to a core by this process is approximately twenty (20) milligrams per inch length (2.5 cm), for a thirty percent (30%) solution. The active solution strengths for from 8% water soluble agent to 50% water soluble agent.

After the core is dry, it is wrapped with a fabric substrate 16 having a reactive fluid prepolymer resin in contact with this fabric. The fabric substrate is made from filaments which can include, but are not limited to, polyester, polypropylene, nylon, aramid, polyethylene, polytetrafluoroethylene, polyvinylchloride, polyvinylidiinechloride, acrylic, polystyrene, polyethylene terephthalate, polyurethane, fiberglass, polyaramid, ceramic, graphite, boron, stainless steel, cotton, ramie, linen, hemp, silk, flax and mixtures thereof. An example of a suitable fabric would be a Raschal Knit fiberglass fibers. The orthopedic casting material reactive fluid prepolymer is preferably a polyisocyanate prepolymer which hardens when said resin is wetted in water.

In practice tack from a water activated resinous prepolymer material in the application of an orthopedic cast can be reduced facilitating the process. The fabric substrate, coated with a water activated resinous prepolymer material, wrapped about a core coated with a water soluble agent, is packaged and provided in a vacuum package. Before the casting process, the applicator fills a container with water, forming a water bath. The substrate wrapped core is removed from the vacuum package and immersed in the container of water. Once the core about which the resin coated substrate is wrapped is exposed to water, the lubricant is transferred by the water to the outside portion of the cast tape, reducing the tackiness of the cast tape, thereby facilitating its overall handling. This transfer is very limited in nature and only puts the lubricant in contact with the cast tape at the point which will be used to form the outer most layer of the cast.

Figure 3:
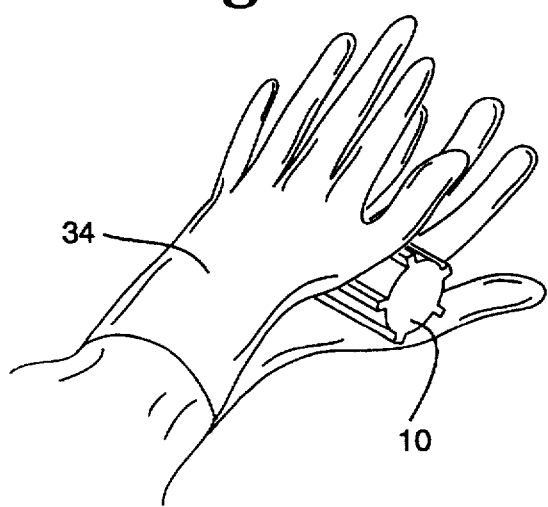
FIG. 3 is an isometric view of wet gloved hands in contact with the core to release the water soluble agent to the gloves.
Figure 4:
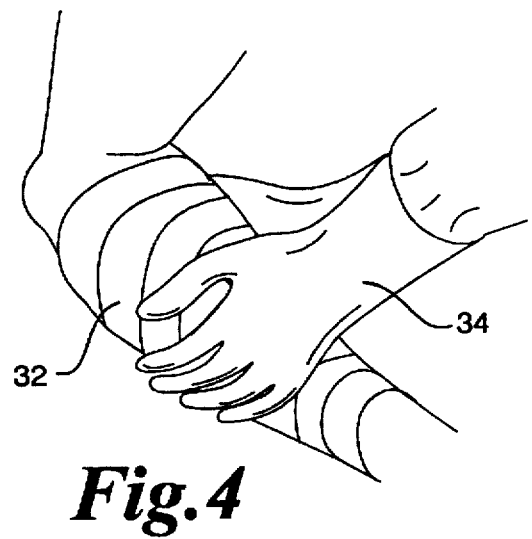
FIG. 4 is an isometric view of the application of an arm cast with gloves.

During the shaping and smoothing of the cast 32, FIG. 4, the applicator's gloves 34 can start to become tacky or sticky, inhibiting the molding process. This can be reduced by wetting the gloves and the core 10 in the container of water and bringing the wetted gloves 34, FIG. 3, in contact with the wetted core thereby releasing additional water soluble agent to the gloves. This limited transfer only puts the lubricant in contact with the gloves, which transfer the agent to cast tape at the outer most layer of the cast where it is needed.

ALTERNATIVE EMBODIMENTS

The elongated core has an exterior surface and can optionally be configured with at least one ridge 22, FIG. 1, extending from the exterior surface. These ridges preferably run longitudinally the length of the core, as shown in FIG. 1.

Figure 5:
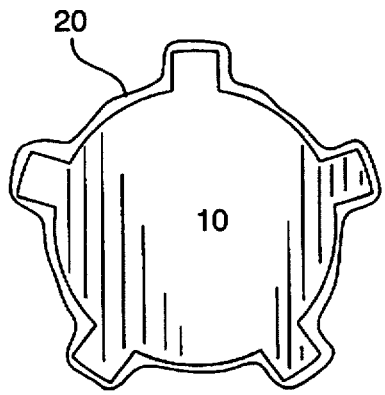
FIG. 5 is a side view of the core with a film of the water soluble agent.

The core can be configured as a non-water permeable tube 24, FIG. 7, which increases the overall surface area 18 by including the interior surface 26 of the tube. Therefore through the same application technique more water soluble agent can be added. Ridges 22 can also be added to this configuration, 28, FIG. 8. While the tubes and cores shown in the drawings are generally round or cylindrical, 30, FIG. 9, one of ordinary skill in the art will understand that the tubes can be configured to have cross sectional shapes which include, but are not limited to, square, oval, oblong, triangular, pentagonal and octagonal. The tubes can have closed ends as shown in FIGS. 5 and 6, or can be open ended as shown in FIGS. 7 and 8.

EXAMPLES

Example 1

The three inch (3 inch, 8 cm) long cores were dipped into a thirty percent (30%) active solution of sodium lauryl sulfate (SLS), the remainder of the solution being water. The cores were allowed to drain by standing them on one end for twenty four (24) hours. The average amount of sodium lauryl sulfate added to the cores was about fifty (50) milligrams for a enclosed elongated core as shown in Table 1.

TABLE 1

| Enclosed Core (30% SLS) | | | |
| --- | --- | --- | --- |
| Number | Core Weight (g) | Weight of Core & SLS (g) | SLS Weight (g) |
| 1 | 5.0611 | 5.1037 | 0.0426 |
| 2 | 4.9463 | 5.0085 | 0.0622 |
| 3 | 5.0216 | 5.0857 | 0.0641 |
| 4 | 4.9036 | 4.9796 | 0.0760 |
| 5 | 5.0134 | 5.0361 | 0.0227 |
| 6 | 4.9763 | 5.0357 | 0.0594 |

TABLE 1-continued

Enclosed Core (30% SLS)

| Number | Core Weight (g) | Weight of Core & SLS (g) | SLS Weight (g) |
| --- | --- | --- | --- |
| 7 | 4.9899 | 5.0370 | 0.04710 |
| 8 | 4.9436 | 5.0108 | 0.0672 |
| 9 | 4.9353 | 4.9918 | 0.0565 |
| 10 | 5.0003 | 5.0453 | 0.0450 |
| 11 | 5.0765 | 5.1174 | 0.0409 |
| 12 | 4.9423 | 5.0041 | 0.0618 |
| 13 | 4.9306 | 5.0024 | 0.0718 |
| Average | 4.9801 | 5.0352 | 0.0552 |

One can also use an open-ended non-water-permeable tube which increases the overall surface area by including the interior surface of the tube. Therefore through the same application technique more water soluble agent can be added. Using the technique described above, open-ended tubes three inches (3 inch, 8 cm) long, having a half-inch outside diameter (0.500 inch, 1.3 cm OD), were dipped into a thirty percent (30%) active solution of sodium lauryl sulfate (SLS) and allowed to stand for twenty four hours. The average amount of sodium lauryl sulfate added to the cores was about eighty (80) milligrams for an open-ended elongated core as shown in Table 2.

TABLE 2

Tube Core half inch diameter (.500 inch, 1.3 cm OD) (30% SLS)

| Number | Core Weight (g) | Weight of Core & SLS (g) | SLS Weight (g) |
| --- | --- | --- | --- |
| 1 | 3.6671 | 3.7682 | 0.1011 |
| 2 | 3.8016 | 3.8991 | 0.0975 |
| 3 | 3.5552 | 3.6438 | 0.0886 |
| 4 | 3.6307 | 3.6881 | 0.0574 |
| 5 | 3.5483 | 3.6174 | 0.0691 |
| 6 | 3.5652 | 3.6359 | 0.0707 |
| Average | 3.6280 | 3.7088 | 0.0807 |

Example 2

Using the technique described above an open ended tube, three inches (3 inch, 8 cm) long, having a half inch outside diameter (0.500 inch, 1.3 cm OD), is dipped into an eighteen percent (18%) active solution of sodium lauryl sulfate (SLS) and allowed to stand for twenty four hours. The average amount of sodium lauryl sulfate added to the cores was about twenty (20) milligrams for an open-ended elongated core as shown in Table 3.

TABLE 3

Tube Core half inch diameter (.500 inch, 1.3 cm OD) (30% SLS)

| Number | Core Weight (g) | Weight of Core & SLS (g) | SLS Weight (g) |
| --- | --- | --- | --- |
| 1 | 3.5516 | 3.5757 | 0.0241 |
| 2 | 3.6122 | 3.6289 | 0.0167 |
| 3 | 3.5167 | 3.5388 | 0.0221 |
| 4 | 3.6640 | 3.6827 | 0.0187 |
| 5 | 3.5728 | 3.5912 | 0.0184 |
| Average | 3.5835 | 3.6035 | 0.0200 |

SUMMARY OF THE ACHIEVEMENT OF THE OBJECTS OF THE INVENTION

From the foregoing, it is readily apparent that we have invented an improved method and apparatus for wrapping and molding an orthopedic cast which reduces the tack of the resin coated substrate. This method of molding and smoothing an orthopedic cast results in less tack and does not appreciably alter the process being utilized by the doctor in the forming of the cast. The invented core's outside surface is coated with a lubricant which facilitates the molding and smoothing of the orthopedic cast. Unlike other systems, the lubricant provided reduces tack but does not interact with the prepolymer system, thereby avoiding reducing the overall strength of the orthopedic cast. This lubricant is also non-toxic and will not cause skin irritation.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. An orthopedic casting material comprising:
   a water-impermeable elongated core coated with a water soluble agent, said water soluble agent selected from the group consisting of alkali salts of fatty acids and compounds having a hydrophobic hydrocarbon end plus a sulfonate or sulfate ionic end;
   a fabric substrate wrapped about said core; and
   a reactive fluid prepolymer resin in contact with said fabric substrate.

2. The orthopedic casting material according to claim 1 wherein said alkali salt of fatty acids is selected from the group consisting of: sodium lauryl sulfate; sodium stearate; sodium palmitate and combinations thereof.

3. The orthopedic casting material according to claim 1 wherein said core has an exterior surface and at least one longitudinal ridge extending outwardly from said exterior surface.

4. The orthopedic casting material according to claim 1 wherein said water soluble agent is sodium lauryl sulfate.

5. The orthopedic casting material according to claim 1 wherein said fabric substrate is made from filaments selected from the group of filaments consisting of: polyester, polypropylene, nylon, aramid, polyethylene, polytetrafluoroethylene, polyvinylchloride, polyvinylidiinechloride, acrylic, polystyrene, polyethylene terephthalate, polyurethane, fiberglass, polyaramid, ceramic, graphite, boron, stainless steel, cotton, ramie, linen, hemp, silk, flax, and mixtures thereof.

6. The orthopedic casting material according to claim 1 wherein said reactive fluid prepolymer resin is a polyisocyanate prepolymer which hardens when said resin is wetted in water.

7. The orthopedic casting material according to claim 1 wherein said core is made from a material selected from the group consisting of: polyester, polypropylene, nylon, aramid, polyethylene, polytetrafluoroethylene, polyvinylchloride, polyvinylidiinechloride, acrylic, polystyrene, polyethylene terephthalate, polyurethane, ureaformaldehyde, phenolics, melamine formaldehydes, modified terephthalates and combinations thereof.

8. The orthopedic casting material according to claim 1 wherein said core is a tube.

9. The orthopedic casting material according to claim 8 wherein said tube has an exterior surface and has at least one ridge extending outwardly from said exterior surface.

* * * * *